United States Patent
Carrafa et al.

(10) Patent No.: US 10,799,109 B2
(45) Date of Patent: Oct. 13, 2020

(54) SYSTEMS AND METHODS FOR DETERMINING DISTANCE FROM AN OBJECT

(71) Applicant: JAND, INC., New York, NY (US)

(72) Inventors: Joseph Carrafa, Brooklyn, NY (US); David Howard Goldberg, New York, NY (US)

(73) Assignee: JAND, Inc., New York, NY (US)

( * ) Notice: Subject to any disclaimer, the term of this patent is extended or adjusted under 35 U.S.C. 154(b) by 335 days.

(21) Appl. No.: 14/996,917

(22) Filed: Jan. 15, 2016

(65) Prior Publication Data

US 2017/0202450 A1 Jul. 20, 2017

(51) Int. Cl.
| | | |
|---|---|---|
| A61B 3/032 | (2006.01) | |
| A61B 3/00 | (2006.01) | |
| A61B 3/028 | (2006.01) | |

(52) U.S. Cl.
CPC ............ *A61B 3/032* (2013.01); *A61B 3/0025* (2013.01); *A61B 3/0033* (2013.01); *A61B 3/0083* (2013.01); *A61B 3/028* (2013.01)

(58) Field of Classification Search
CPC ......... A61B 3/022; A61B 3/028; A61B 3/032; A61B 3/066; A61B 3/0325; A61B 3/0025; A61B 3/0083; A61B 3/0033
USPC ................................ 351/237–239, 243, 246
See application file for complete search history.

(56) References Cited

U.S. PATENT DOCUMENTS

| | | | |
|---|---|---|---|
| 9,549,669 B2 | 1/2017 | Limon | |
| 2007/0021869 A1 | 1/2007 | Baek | |
| 2008/0101784 A1 | 5/2008 | Hsu | |
| 2012/0050686 A1 | 3/2012 | Bartlett et al. | |
| 2013/0169801 A1 | 7/2013 | Martin et al. | |
| 2014/0268060 A1 | 9/2014 | Lee et al. | |
| 2014/0300722 A1* | 10/2014 | Garcia | G01B 11/02 348/77 |
| 2016/0120402 A1* | 5/2016 | Limon | A61B 3/032 351/241 |

(Continued)

FOREIGN PATENT DOCUMENTS

| | | | | |
|---|---|---|---|---|
| WO | 20120138355 | 10/2012 | | |
| WO | WO2015197149 | * 12/2015 | ............ | A61B 3/032 |

(Continued)

OTHER PUBLICATIONS

International Search Report and the Written Opinion of the International Searching Authority from corresponding PCT/US2017/012804 dated Apr. 12, 2017.

(Continued)

*Primary Examiner* — Marin Pichler

(74) *Attorney, Agent, or Firm* — Duane Morris LLP

(57) ABSTRACT

A process is provided for conducting an eye examination using a mobile device, the process comprising capturing a first image of an object using a camera of a mobile device set to a fixed focusing distance; determining, with reference to the first image, an absolute size of the object; capturing a second image of the object using the camera of the mobile device; determining, with reference to the second image, a distance from the mobile device to the object; providing an indication via the mobile device to move the mobile device relative to the object; and receiving input from the mobile device in response to the eye examination program.

18 Claims, 9 Drawing Sheets

(56) References Cited

U.S. PATENT DOCUMENTS

2017/0079523 A1    3/2017  Limon
2017/0135571 A1*   5/2017  Schubart ................ A61B 3/032

FOREIGN PATENT DOCUMENTS

WO    WO-2016181308 A1    11/2016
WO    WO-2016181309 A1    11/2016
WO    WO-2016181310 A1    11/2016
WO       20160196803      12/2016

OTHER PUBLICATIONS

International Preliminary Report on Patentability for PCT/US2017/012804, dated Jul. 17, 2018, 4 pages.
Canadian Office Action for Application No. 3011428, dated Mar. 1, 2019, 4 pages.
Canadian Office Action for Application No. 3011428, dated Sep. 20, 2019, 4 pages.
Extended European Search Report for EP App. No. 17738787.5-1124 dated Jul. 29, 2019, 6 pages.

* cited by examiner

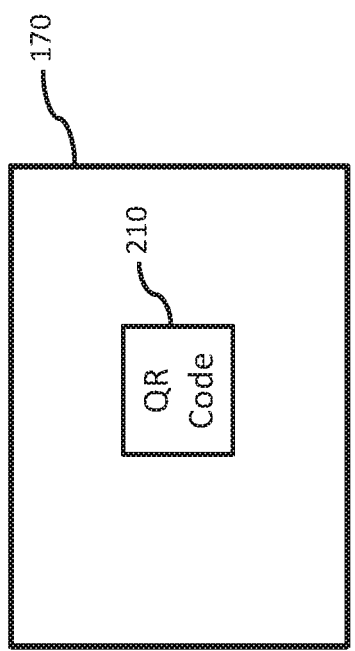
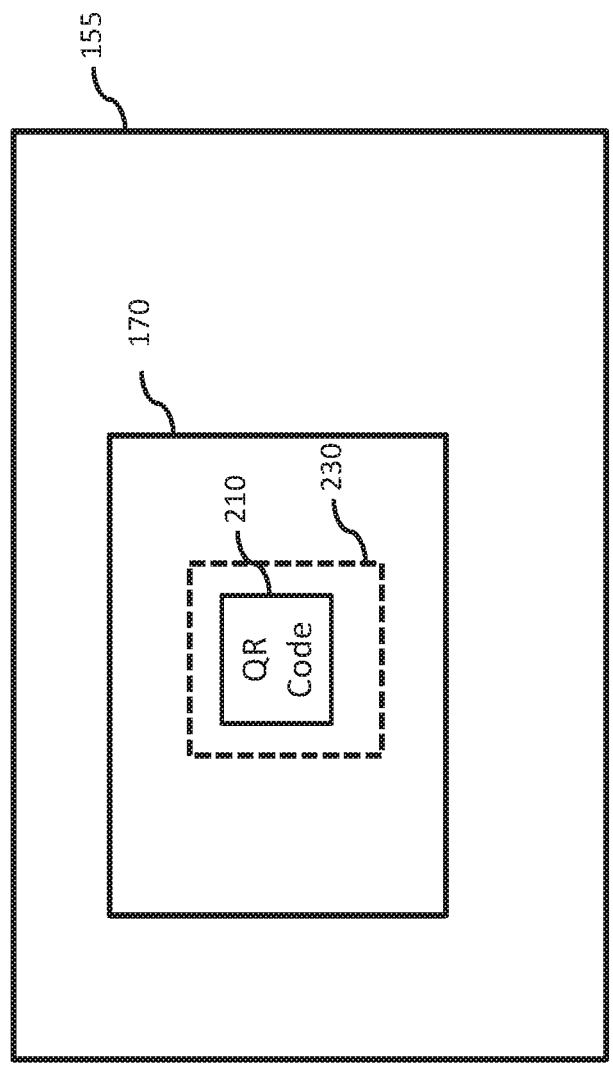

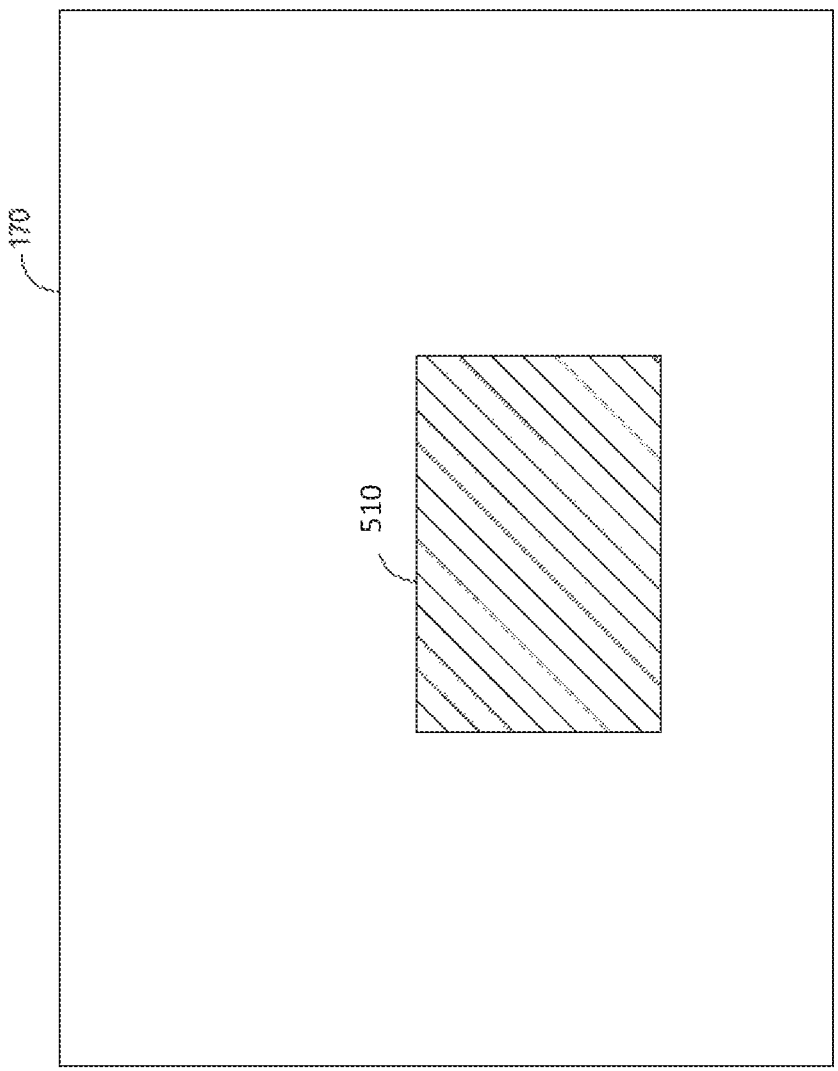

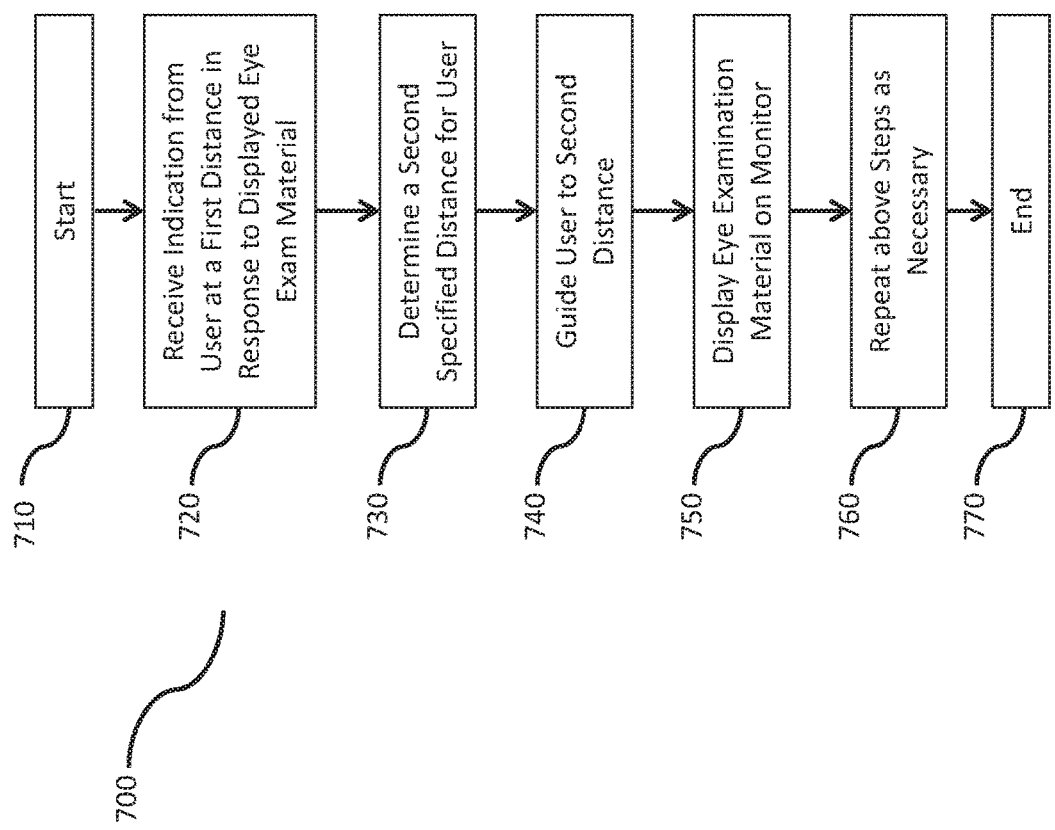

SYSTEMS AND METHODS FOR DETERMINING DISTANCE FROM AN OBJECT

BACKGROUND

Technical Field

The technical field generally relates to distance determination, and more particularly, in one aspect, to systems and methods for calculating user distance from an object during an eye examination.

Background Discussion

Eye examinations are routinely used to determine the appropriate lens prescription for patients. One variable that must be known to perform an effective eye exam is the distance between a test subject and the displayed eye test. Eye exams have traditionally been performed by optometrists or the like in an office where a set distance from the patient to an eye chart or other testing material is easily maintained. Efforts to translate eye exam procedures from a doctor or technician's office to non-traditional locations such as self-administered tests at home are hampered by the difficulties associated with a user's ability to determine with confidence his or her distance from the testing material so that reliable results may be obtained. Proposed solutions such as using measuring tape or counting steps to determine a distance from a computer screen displaying an eye test require additional equipment or steps and may erode a user's confidence in the results, making a test administered out of office less attractive.

SUMMARY

According to one aspect of the present invention, a process for conducting an eye examination using a mobile device is provided comprising capturing a first image of an object using a camera of a mobile device set to a fixed focusing distance, determining, with reference to the first image, an absolute size of the object, capturing a second image of the object using the camera of the mobile device, determining, with reference to the second image, a distance from the mobile device to the object, providing an indication via the mobile device to move the mobile device relative to the object, and receiving input from the mobile device in response to the eye examination program. According to one embodiment, the object is an optotype displayed in connection with the eye examination program. According to one embodiment, the object is a test pattern. According to one embodiment, determining, with reference to the first image, an absolute size of the object further comprises determining a first image size of the object in the first image. According to another embodiment, determining, with reference to the first image, an absolute size of the object is performed with reference to the first image size of the object in the first image, a focal length of the camera of the mobile device, a second distance between the lens and the focal plane of the camera, and a third distance from the lens at which the object is in optimal focus.

According to one embodiment, determining, with reference to the second image, a distance from the mobile device to the object further comprises determining a second image size of the object in the second image. According to one embodiment, determining, with reference to the second image, a distance from the mobile device to the object is performed with reference to the second image size of the object in the second image, the absolute size of the object, and the focal length of the camera of the mobile device.

According to one embodiment, providing an indication via the mobile device to move the mobile device relative to the object comprises providing an indication via the mobile device to move the mobile device in a direction relative to the object. According to an alternative embodiment, providing an indication via the mobile device to move the mobile device relative to the object comprises providing an indication via the mobile device to move the mobile device to a second distance from the object. According to another embodiment, the second distance corresponds to an optimal distance for conducting an eye examination test.

According to another aspect of the present invention, a mobile device is provided comprising a camera, a visual display, and a processor coupled to the camera, the processor configured to capture a first image of an object using the digital camera, determine, with reference to the first image, an absolute size of the object, capture a second image of the object using the digital camera, determine, with reference to the second image, a distance from the mobile device to the object, provide an indication via the display to move the mobile device relative to the object, and receive input from a user of the mobile device in response to an eye examination program. According to one embodiment, determining, with reference to the first image, an absolute size of the object further comprises determining a first image size of the object in the first image. According to one embodiment, the camera comprises a lens having a focal length and a focal plane, wherein determining, with reference to the first image, an absolute size of the object is performed with reference to the first image size of the object in the first image, the focal length, a second distance between the lens and the focal plane, and a third distance from the lens at which the object is in optimal focus. According to another embodiment, determining, with reference to the second image, a distance from the mobile device to the object further comprises determining a second image size of the object in the second image.

According to an alternative embodiment, the camera comprises a lens having a focal length, wherein determining, with reference to the second image, a distance from the mobile device to the object is performed with reference to the second image size of the object in the second image, the absolute size of the object, and the focal length. According to one embodiment, providing an indication via the display to move the mobile device relative to the object comprises providing an indication via the display to move the mobile device in a direction relative to the object. According to one embodiment, providing an indication via the display to move the mobile device relative to the object comprises providing an indication via the display to move the mobile device to a second distance from the object. According to another embodiment, the second distance corresponds to an optimal distance for conducting an eye examination test.

Still other aspects, embodiments, and advantages of these exemplary aspects and embodiments, are discussed in detail below. Moreover, it is to be understood that both the foregoing information and the following detailed description are merely illustrative examples of various aspects and embodiments, and are intended to provide an overview or framework for understanding the nature and character of the claimed subject matter. Particular references to examples and embodiments, such as "an embodiment," "an example," "one example," "another embodiment," "another example," "some embodiments," "some examples," "other embodiments," "an alternate embodiment," "various embodiments," "one embodiment," "at least one embodiments," "this and other embodiments" or the like, are not necessarily mutually exclusive and are intended to indicate that a particular feature, structure, or characteristic described in connection with the embodiment or example and may be included in that embodiment or example and other embodiments or examples. The appearances of such terms herein are not necessarily all referring to the same embodiment or example.

Furthermore, in the event of inconsistent usages of terms between this document and documents incorporated herein by reference, the term usage in the incorporated references is supplementary to that of this document; for irreconcilable inconsistencies, the term usage in this document controls. In addition, the accompanying drawings are included to provide illustration and a further understanding of the various aspects and embodiments, and are incorporated in and constitute a part of this specification. The drawings, together with the remainder of the specification, serve to explain principles and operations of the described and claimed aspects and embodiments.

BRIEF DESCRIPTION OF DRAWINGS

Various aspects of at least one embodiment are discussed below with reference to the accompanying figures, which are not intended to be drawn to scale. The figures are included to provide an illustration and a further understanding of the various aspects and embodiments, and are incorporated in and constitute a part of this specification, but are not intended as a definition of the limits of any particular embodiment. The drawings, together with the remainder of the specification, serve to explain principles and operations of the described and claimed aspects and embodiments. In the figures, each identical or nearly identical component that is illustrated in various figures is represented by a like numeral. For purposes of clarity, not every component may be labeled in every figure. In the figures:

FIGS. 2A and 2B are illustrations of a user interface during a device pairing step according to one or more embodiments;

FIG. 5 is an illustration of a user interface during an object size determination step according to one or more embodiments;

FIG. 7 is a flow chart of a method for repositioning a test subject according to one or more embodiments;

DETAILED DESCRIPTION

Figure 1:
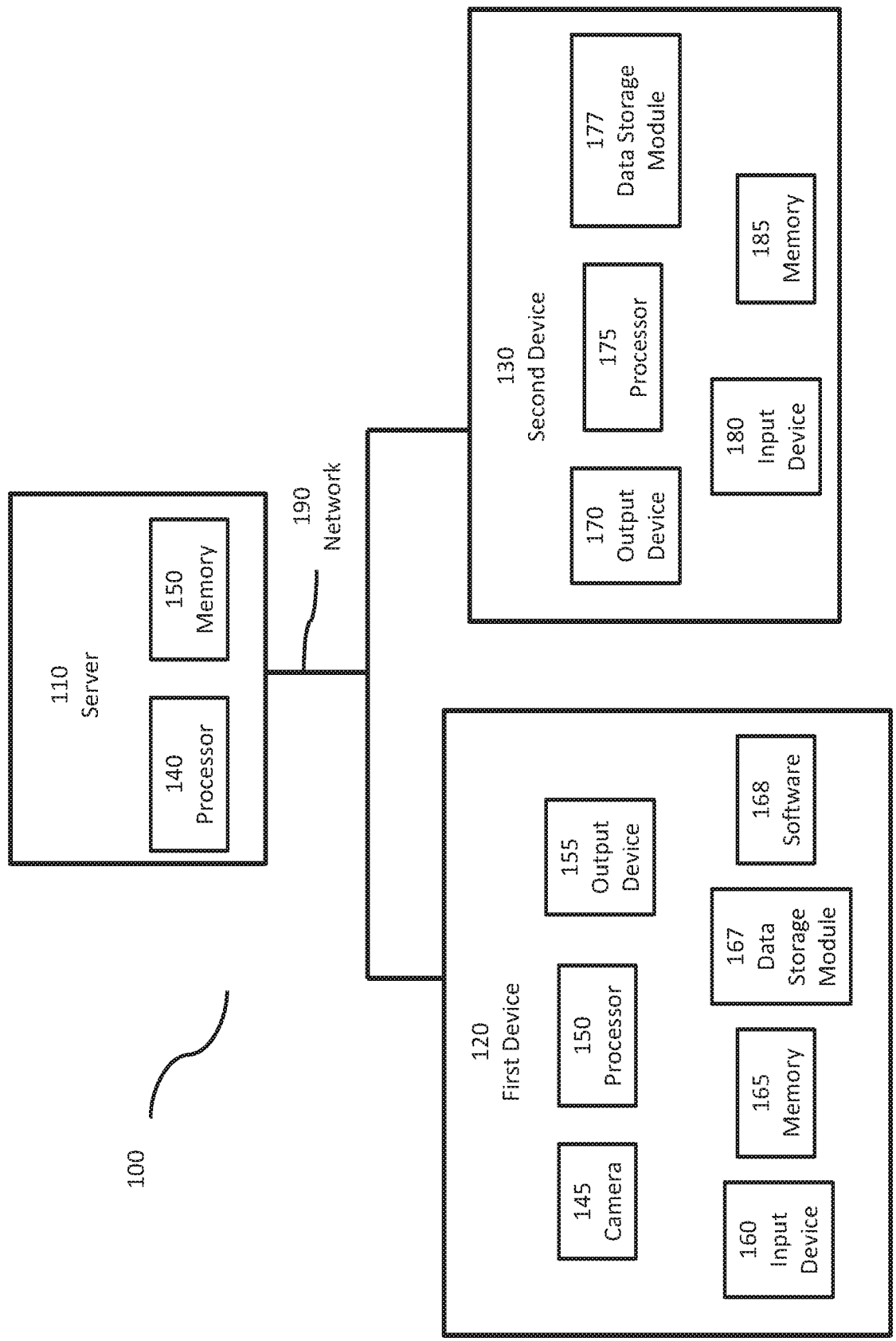
FIG. 1 is a block diagram of a range-finding system according to one or more embodiments.

According to one or more embodiments, the methods and systems disclosed allow a person to easily determine their distance from an object. In one embodiment, the target object is an image of a pattern, an eye exam, or other suitable item. The image may be displayed on a computer screen or other suitable medium such as a printed sheet or series of printed sheets.

According to one or more embodiments, the disclosed methods and systems may guide a person to a specific distance from the object. The provided guidance may facilitate a user to undergo an eye exam without the need for technical or trained personnel to administer the test. As such, this disclosure creates the potential for a range of people to receive an accurate eye exam who may have difficulty accessing an optometrist's office (those that are infirm, remote, etc.), or those who may prefer the convenience of a remotely-administered exam.

According to one or more embodiments, the distance from an object (e.g., a pattern displayed as part of an eye examination) is determined by using a camera capable of running custom software and, according to some examples, displaying feedback to the user (such as may be provided by a smartphone or other mobile or portable device, such as a tablet or laptop computer). According to one or more embodiments, the methods provided do not require specific information about the camera and can be run on most consumer mobile phones or any portable computing device that includes a camera.

According to one or more embodiments, certain intrinsic and extrinsic properties of the camera may be retrieved from a data store prior to or during a distance-finding process. For example, the pixel pitch of the screen of the mobile device, the focal length of the camera, the best-focus distance (the distance between the lens of the camera, set to a fixed focus, and the location at which an object would appear optimally in focus), and the distance between the lens and the focal plane may be treated as constant across all smartphones of a particular model, and may be considered as properties of the camera. Such properties may be determined, for example, in a laboratory, once for each type of mobile device, and the properties made available for use in the methods and systems described herein. In some embodiments, the intrinsic and extrinsic properties may be stored on the mobile device itself as part of a configuration or metadata file. Alternatively, calibration may be performed by the user to determine the camera's intrinsic and extrinsic properties. Calibration of the camera on the mobile device may be carried out according to any methods known to a person of ordinary skill in the art. According to one or more embodiments, calibration requires images of the calibration pattern from multiple angles to determine camera properties. As such, better calibration results can be achieved closer to the pattern where the camera can be moved at a greater angle. In the case that the camera device has other sensors such as an accelerometer, those sensors may be used to make calibration faster or more accurate.

According to one or more embodiments, a user may begin the process for determining a distance for an eye examination while positioned near a displayed calibration pattern; the user runs the application, and points the camera at the calibration pattern. The user then engages in a process for determining the absolute size of the calibration pattern. The process may involve fixing the camera focus (e.g., to the nearest possible focus) and capturing images of the calibration pattern with the camera at various distances from the pattern. Images may be captured automatically at fixed intervals or upon the occurrence of certain events (such as the camera being held still, the camera being moved a certain amount as detected by an accelerometer, etc.) or may be captured by the user touching an interface element on the screen or otherwise manually indicating that an image should be captured.

The calibration pattern may be an object with a known geometry and easily detectable feature points. According to some embodiments a chessboard pattern is used. Calibration aids in relating pixel count of an object to actual dimensions. The absolute size of the calibration pattern on the sensor of the camera can be determined by multiplying the size of the calibration pattern in pixels in an image by the pixel pitch (the distance from the center of one pixel to the center of a neighboring pixel) of the sensor. Some or all of the known intrinsic qualities of the camera (such as the focal length, best-focus, distance, and distance between the lens and the focal plane) may be factored with the image size of the object to determine the actual size of the object.

Once the absolute size of the calibration pattern has been determined, the distance between the pattern and a location of the camera may be determined with reference to the image size of the pattern in an image captured at the location. One may then accurately track the distance from the target to the camera as one is moved in relation to the other.

According to one or more embodiments, the pattern is presented on an electronic display. However, any medium for the pattern, including paper, can be used. Furthermore, the calibration pattern and the eye exam chart may be displayed on the same monitor or on separate displays, and may be collectively referred to as an object or target object. Unless stated otherwise, references to eye exam material and eye exam chart may be understood to encompass any image, static or dynamic, associated with determining one or more characteristics of a test subject's vision.

In the case where the calibration pattern is on a piece of paper, all instruction can be given through the mobile device. The pattern itself or an eye chart can be used as a target during the tracking stage, during which the camera is moving. In the case where the chessboard pattern is on a computer screen, after calibration the screen can be changed to solid white so that the target is large and is not blurred by lighting contrast or glare as the camera of the mobile device is moved.

In the case where the calibration pattern is displayed on a computer screen, the mobile device can be linked to a web page or application running on the computer such that the mobile device can be used to control the application on the computer. This can be helpful for guiding the user through the calibration process and also for guiding the user through an eye exam. In other embodiments, the mobile device and the computer are not in direct communication with each other, beyond the fact that each may be capable of communicating with the server.

FIG. 1 illustrates a block diagram of an eye examination system 100 according to one or more embodiments. In the embodiment shown in FIG. 1, the system 100 comprises a server 110 in communication with a first device 120 and a second device 130. As shown, the first device 120 is coupled to, and can exchange data with, server 110 and second device 130 via network 190. In addition, according to this example, the first device 120 includes a camera 145, a processor 150 coupled to the camera, an output device 155, such as a monitor or display screen or audio speaker, an input device 160, such as a touch surface, a keyboard, microphone, or a mouse, a data storage module 167, and a memory 165 coupled to the processor 150. The first device 120 also includes camera calibration and eye examination software 168.

The server 110 includes one or more computing devices located remote or local to the first and second devices 120 and 130. The server includes a processor 140 and a memory 142 coupled to the processor. In one example, the memory 142 includes volatile memory, such as RAM, and non-volatile memory, such as a magnetic disk.

The second device 130 includes processor 175, a data storage module 177, a memory 185 coupled to the processor 175, an output device 170, such as a monitor or display screen or audio speaker, and an input device 180, such as a touch surface, a keyboard, microphone, or a mouse. In some embodiments, the first device 120 is a portable computing device. For example, the first device 120 may be a mobile device, such as a smart phone, tablet, or laptop computer, all of which are encompassed by the terms "portable computing device" or "mobile device." The mobile device 120 is capable of delivering and/or receiving data to or from server 110. The second device 130 may be a portable computing device, like any of those described for the first device 120, or a stationary computing device. Unless specified otherwise, the terms "monitor" or "display screen" may be understood to encompass any visual display associated with a portable or stationary computing device.

The server 110 exchanges data with the first and second devices 120 and 130. This data may be exchanged through an installed program in the first or second device 120 or 130, or through a web page loaded on the first or second device 120 or 130.

In use, the first and second devices 120 and 130 may be used in conjunction to determine the distance between the two devices. In one embodiment, the output display 170 of the second device 130 may be used to display a calibration pattern, a substantially blank screen for distance tracking, and/or an eye examination chart. The images displayed on the monitor 170 may be provided to the monitor 170 by the server 110 in response to instructions received from the server 110, and the particular instructions provided to the monitor 170 may be based on information received from the first device 120.

A pairing of the first and second devices 120 and 130 may facilitate their coordination. In one embodiment, the first device 120 may be paired with the second device 130. Such a pairing may facilitate the coordination of instructions and information between the devices. Once paired, the server 110 may deliver instructions to the second device 130 directing what images are displayed on its monitor 170 in response to information received from the camera 145 of the first device 120. The step of pairing may be achieved by any technique known to one of ordinary skill in the art that will allow the server 110 to associate the first device 120 with the second device 130. For example, an identifier may be displayed on the second device 130 and captured by the camera of first device 120 or vice versa. In some embodiments, a QR code or other optical code is displayed on the monitor 170. The camera then captures an image of the code and transmits it to the server 110, allowing the server 110 to match the two devices 120 and 130 and coordinate the instructions sent to each.

FIGS. 2A and 2B illustrate user interfaces during device pairing according to one or more embodiments in which the second device comprises a computer having a monitor 170. In FIG. 2A, the monitor 170 of computer 130 displays a QR code 210. In FIG. 2B the viewfinder 155 of camera 145, which may be displayed on the output device 155, displays the image of the monitor 170 with the QR code 210 within. The code 210 is positioned within the viewfinder's target box 230. The code is identified and the two devices 120 and 130 are paired so that output and input between the two devices 120 and 130 may be coordinated. In one embodiment, the QR code may be generated by the server 110 and provided to the second device 130, while in other embodiments, the second device 130 may generate the QR code and provide it to the server 110. In other embodiments, images other than QR codes may be used to pair the devices, and other identifiers may also be used. For example, a string of letters and or numbers can be displayed on one of devices 120 and 130, and entered in the other of the devices 120 and 130 to pair the devices.

The second device 130, as shown in FIG. 1, is Internet-enabled, and the various patterns, images, or testing material displayed may be provided through a webpage, in response to output from the first device 120. In alternative embodiments, an application or program running on the computer 130 provides the displayed content.

Figure 3:
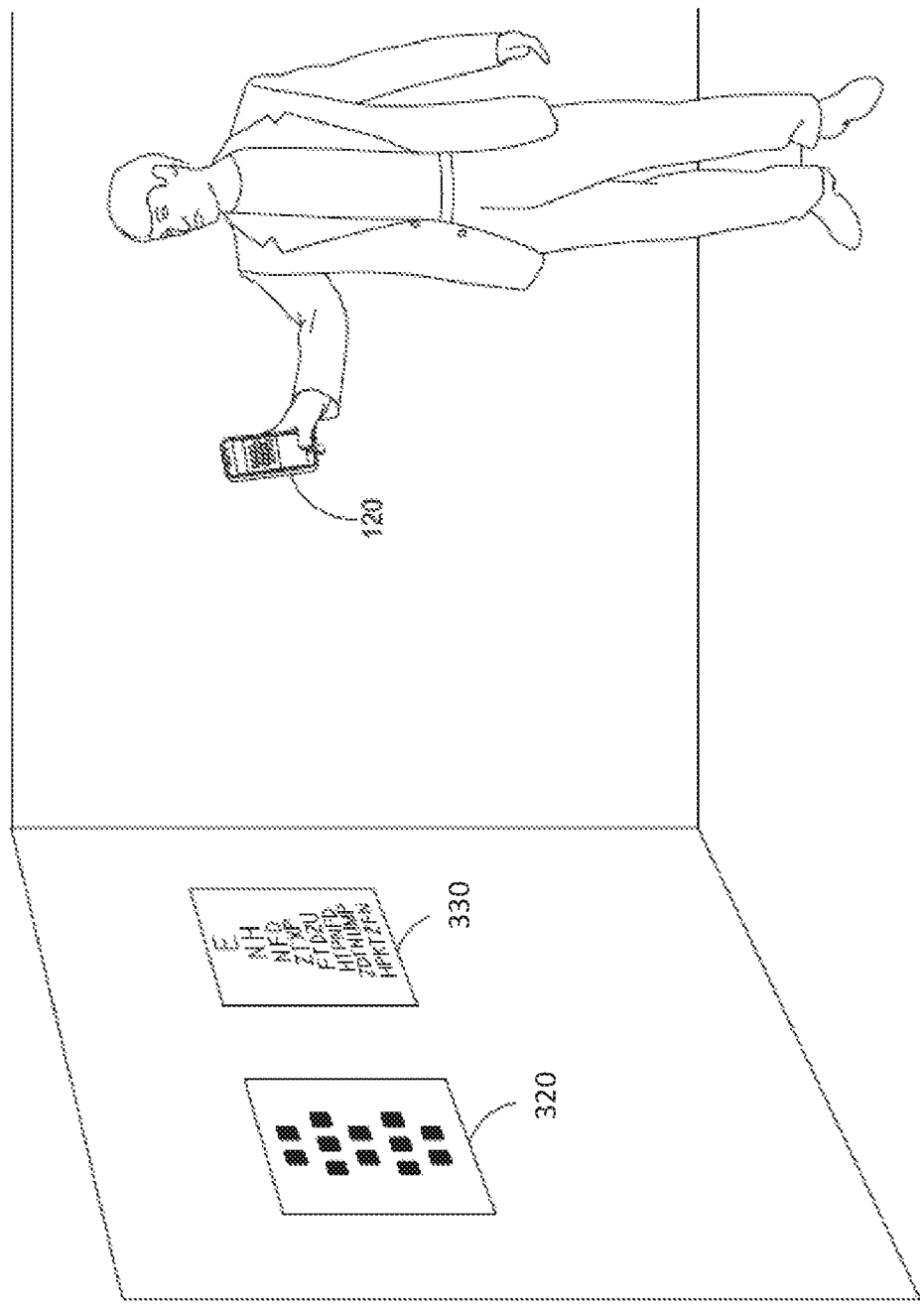
FIG. 3 is an illustration of an embodiment in which a calibration chart and an eye exam chart are displayed on printed paper.

While FIG. 1 shows both the first device 120 and the second device 130 in communication with the server 110, alternative configurations are also within the scope of the present disclosure. In some embodiments, pairing of the first device 120 and the second device 130 is not performed. According to certain embodiments, the first device 120 and/or the second device 130 may not be in communication with a server 110 or each other. For example, all the instructions required by the camera device 120 may already be stored on device 120. Likewise, information or instructions for what to display on the second device 130 may be provided without requiring communication over a network. Also, the second device 130 may be in direct communication with the first device 120 using any of a number of known wireless protocols, such as WiFi or Bluetooth. Furthermore, as discussed elsewhere, in certain embodiments the second device 130 may comprise simply an image printed on a sheet of paper. FIG. 3, for example, shows an alternative, simplified embodiment where the second device comprises a target calibration pattern 320 and eye chart 330 printed out and attached to a wall. A first device 120 having a software-enabled camera is still used to track distance and guide a user to a specified position, and all interaction with the user is done via the first device 120.

Figure 4:
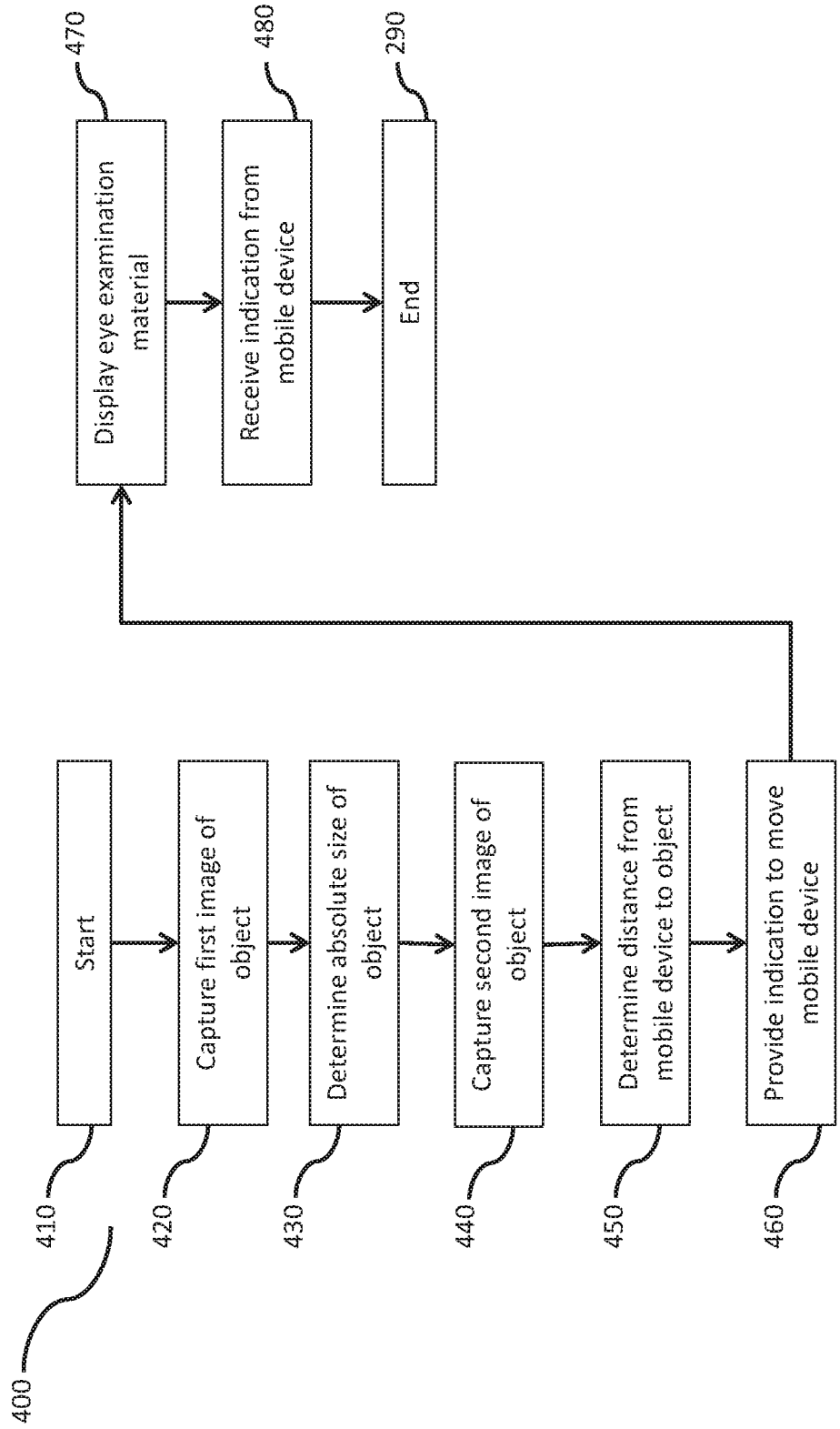
FIG. 4 is a flow chart of a method for determining a distance to an object according to one or more embodiments.

FIG. 4 is a flow chart of a process 400 for determining a distance between a camera of a mobile device and an object displayed on a computer display according to one or more embodiments. One or more embodiments of the process 400 may be implemented using a system such as that shown in FIG. 1.

The process begins at step 410.

At step 420, a first image of an object is captured using a camera of the mobile device. The camera is set to a fixed focusing distance. For example, according to certain embodiments, the camera may be set to a manual focus mode, and the focus may be set to the nearest possible focus point achievable with the camera. In some embodiments, the user is instructed to hold the mobile device with the camera oriented toward the object. An image of the object is then captured by the camera. The image may be captured in response to a user indication, such as clicking a physical button or an interface element on the screen of the mobile device. In other embodiments, the image may be captured automatically once a stable, relatively static image has been obtained and is in focus. For example, an accelerometer of the mobile device may be used to determine that the camera is relatively still. If a focused image can be obtained, the system may attempt to identify the object within the image using known image processing and detection techniques. In some embodiments, multiple images may be captured, and an image may be selected for further processing from among the multiple images based on such criteria as the image in which the object is most in focus, the image in which the object is largest, or the like.

In one embodiment, the object may be an image displayed on a computer display. The object may be a calibration pattern comprising an object with a known geometry and easily detectable feature points. According to some embodiments a chessboard pattern is used. In other embodiments, the object may be an element of an eye examination, such as an optotype comprising a letter, number, or other character or image used to test eyesight during an eye examination.

FIG. 5 is an illustration of a user interface during the step of capturing a first image of the object using the camera of a mobile device. According to the embodiment shown, the computer display 170 includes an object 510 to be captured in an image using the camera of the mobile device. In this example, a user holds the mobile device with the camera oriented toward the computer display 170, including object 510 displayed thereon. The mobile device then captures an image of the object 510.

Returning to FIG. 4, at step 430, an absolute size A of the object is determined with reference to the image captured in step 420. The absolute size is determined with reference to the image size of the object (e.g., the size of the object in pixels or other measure) within the image. In some embodiments, the image size and the absolute size may be scalar values representing the height, width, or other dimension of the image. For example, the image size of the object may be determined by detecting its pixel height, or how many pixels tall the object is as detected by the light sensor of the camera that receives the image. That pixel height may be multiplied by the pixel pitch (a fixed value for a camera that represents the real distance between the centers of two adjoining pixels). The product of pixel height and pixel pitch (in millimeters) yields the image height a of the object (i.e., the size of the object within the image) in millimeters.

The absolute size A of the object (e.g., the physical height of the object as displayed) is determined by the relationship between the image height a of the object and the focal length f of the camera, the best-focus distance $S_1$, and the distance $S_2$ between the lens and the focal plane. In particular, the absolute height A can be determined by the equation:

$$A = \frac{aS_1}{f(1 + S_2/S_1)}$$

The distance $S_2$ between the lens and the focal plane can be derived from the thin lens equation:

$$\frac{1}{f} = \frac{1}{S_1} + \frac{1}{S_2}$$

At step 440, a second image of the object is captured using the camera of the mobile device. As in step 420, the user may be instructed to hold the mobile device with the camera oriented toward the object. The image may be captured in response to a user indication, such as clicking a physical button or an interface element on the screen of the mobile device. In other embodiments, the image may be captured automatically once a stable, relatively static image has been obtained and is in focus. For example, an accelerometer of the mobile device may be used to determine that the camera is relatively still. If a focused image can be obtained, the system may attempt to identify the object within the image using known image processing and detection techniques.

In some embodiments, multiple images may be captured, and an image may be selected for further processing from among the multiple images based on such criteria as the image in which the object is most in focus, the image in which the object is largest, or the like. If the object is not detected in the images, the mobile device may be configured to continue to capture images until the object is detected in an image. Indications as to why the object may not be detected, as well as possible solutions, may be provided to the user via the mobile device. For example, it may be determined and indicated to the user that insufficient or too much lighting is present, or that the camera is not held sufficiently still.

At step 450, the distance from the mobile device to the object is determined with reference to the second image. The image size a' of the object in the second image may be determined, as in step 430, by determining the size in pixels of the object in the image, then multiplying that size in pixels by the pixel pitch of the camera. The absolute height A of the object and the focal length f of the camera are known from previous steps. The arbitrary distance $S'_1$ from the lens of the camera to the object can be determined by the formula:

$$S'_1 = \frac{Af(1 + S_2/S'_1)}{a'}$$

In the case where the object is far enough from the camera, such that $S'_1$ is much larger than $S_2$, the term $S_2/S'_1$ approaches zero. In that case, the distance $S'_1$ can be expressed as:

$$S'_1 = \frac{Af}{a'}$$

Under normal eye examination conditions, the user (and thus the mobile device) is likely to be several feet away from the object, which is sufficiently far that the above formula may be used. It should be noted that this formula for calculating $S'_1$ does not depend on $S_2$, as was required in step 430, meaning that the distance $S_2$ between the lens and the focal plane need not be held constant by maintaining a fixed focus point. The camera may therefore be placed into automatic focus mode for this and subsequent steps, or may remain in manual focus mode.

At step 460, an indication is provided via the mobile device to move the mobile device relative to the object. In an embodiment in which the method is being performed to determine a distance at which a user should take an eye examination, instructions may be provided for the user to move closer to, or further away from, the object (e.g., the eye examination materials) in order to conduct the test at the appropriate distance for the size of the object. The appropriate distance may be determined with reference to the absolute size of the object, as well as the image size of the object in the second image. An eye examination may require the object to appear at a certain size from the user's location during the eye examination, irrespective of the absolute size of the object. For example, at 3 meters, a person with 20/20 vision can read a standard "E" that is 4.36 mm tall on a Snellen chart, while at 6 meters, that letter at 8.73 mm tall would appear to be the same size, and would also be legible to a person with 20/20 vision. The two letters look the same because the angle at which they hit the eye is the same. This angle may be referred to as the visual angle, which is discussed in more detail in U.S. application Ser. No. 14/867,677, titled "SYSTEMS AND METHOD FOR DISPLAYING OBJECTS ON A SCREEN AT A DESIRED VISUAL ANGLE" and filed on Sep. 28, 2015, the contents of which are hereby incorporated by reference in their entirety.

Thus, for a given absolute size of the object, the user may be required to stand in a first location; for an object having a larger absolute size, the user may be required to move further away from the eye examination materials (i.e., the object) in order to maintain the visual angle of the object for consistent results. The appropriate distance may be determined with reference to the formula for determining the visual angle, or may be determined from a data store (e.g., a table) correlating absolute size of the object with the corresponding appropriate distance for conducting an eye examination involving that object.

The mobile device may guide the user holding the mobile device 120 to a specific distance from the computer display 170. Guidance may comprise providing an indication to the user equipped with the mobile device 120 of the current distance from the computer display 170, as determined in step 450. Guidance may further comprise providing an indication of the user's location in relation to a specified end-point distance that the user is attempting to reach, to aid the user in determining where to move in relation to the monitor 170. Guidance may further comprise providing instructions to the user to continue to move to or from the computer display 170. These instructions may be provided on the computer display 170 or on a display of the mobile device, or conveyed audibly.

The specific distance from the monitor that the user is attempting to reach may be a fixed distance determined as required by the particular application. In the context of providing an eye examination, a particular eye test may require that the user be at a specific distance, for example ten feet from the computer displaying an eye chart, give or take some acceptable range of error, which may be one foot or ten percent of the total distance according to certain embodiments. Alternatively, the specific distance may be a function of the displayed object size determined in step 430. Where the displayed object is found to be smaller, the specified end-distance from the monitor may be shorter, as the items displayed on the monitor will be smaller. Alternatively, the results of step 430 may be used to display letters of a fixed size, allowing the same distance to be used regardless of the screen size.

As the mobile device is moved in relation to the computer display 170, the designated distance from the screen 170 may ultimately be reached. Step 460 of the process 400 includes providing an indication to a user once the designated distance has been reached. The indication may be a display on the computer display 170 or on the mobile device of any general type that would inform a user to stop moving in relation to the computer display.

Figure 6A:
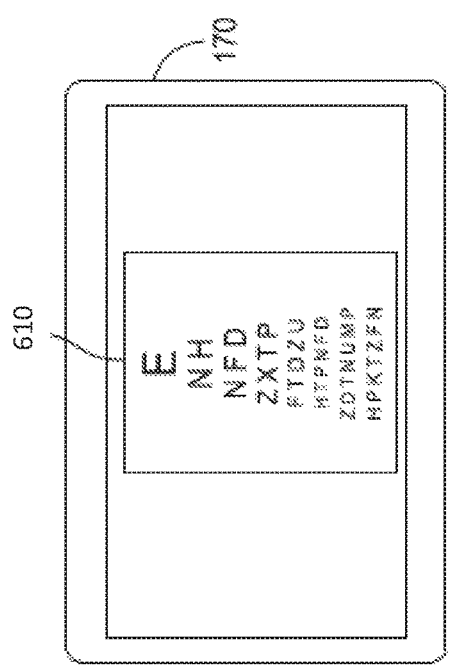
FIGS. 6A and 6B are illustrations of a user interface during a step of indicating that a designated distance has been reached according to one or more embodiments.
Figure 6B:
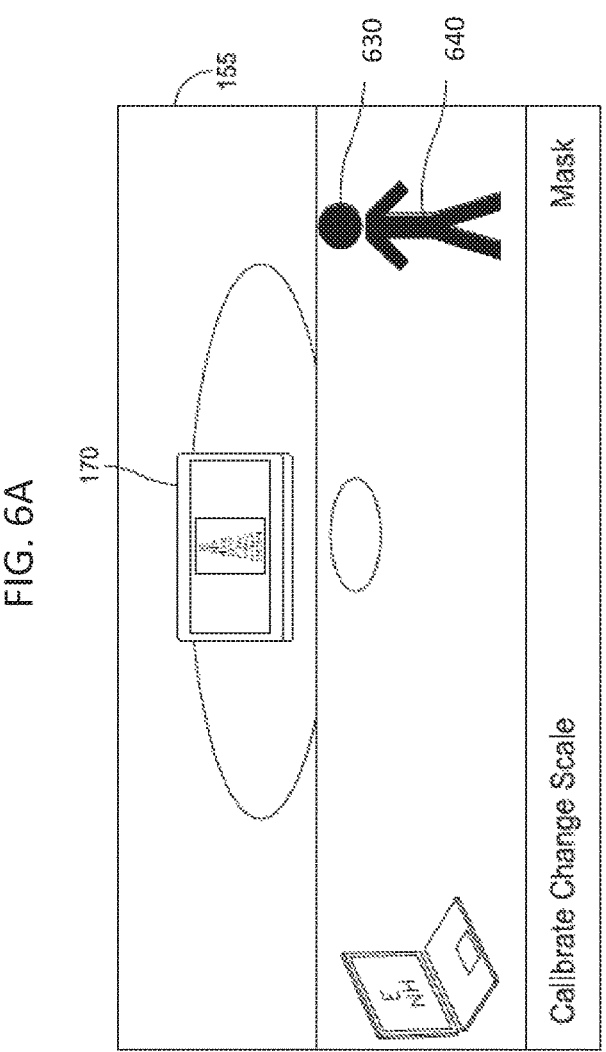

FIGS. 6A and 6B are illustrations of a user interface during a step of indicating that a designated distance has been reached, according to one or more embodiments. In FIG. 6A computer display 170, which is paired with the mobile device, displays an eye chart 610 to indicate the specified distance has been reached. FIG. 6B illustrates a display on the mobile device. In addition to maintaining the computer display 170 in the camera viewfinder, the mobile device also displays a current distance 650 from the monitor 170 and shows superimposed icons 630 and 640 of a person standing at the desired distance and of the user, respectively, thereby providing indication that the specified distance has been reached. In some embodiments, the appearance of the icon 640 may change (e.g., by changing color from red to green) to indicate that the specified distance has been reached.

In the context of an eye examination, the distance from the eye to the eye test chart may be slightly different from the distance between the camera and the testing display depending on the positioning of the camera by the user relative to the user's eyes. In some embodiments, the user may be instructed to position the camera near the user's eyes to reduce this error, or the system may include an adjustment to the measurement distance based on a typical distance between the position at which the user holds the camera and the user's eyes. Unless stated otherwise, the phrase "specified distance" and related terms are understood to include a distance within a reasonable range of error. According to some embodiments, the range of error may be one foot or ten percent of the total distance, whichever is greater.

Returning to FIG. 4, at optional step 470, eye examination material is displayed on the computer display 170 and the eye test or a new phase of the eye test may begin. In embodiments which include a step of pairing the mobile device to the computer 130, the eye exam material may automatically be displayed once the designated distance is reached. A variety of different eye tests may be implemented in step 470, depending on the needs of the user. Tests may include: tests of visual acuity; both cylindrical power and spherical power tests; tests for peripheral vision or color blindness; tests for astigmatism, cataracts and various pathologies or diseases, etc. Tests may be static or dynamic. Specific examples of testing material include, without limitation, Snellen charts, E charts, Landoldt C charts, and the like. The disclosed embodiments may also be particularly useful for eye examination protocols in which the user's distance from the eye examination materials is an aspect of the examination. Such tests may include, without limitation, near and far focal point testing, contrast sensitivity tests, near vision testing for acuity, and binocular testing.

At optional step 480, indications are received from the user in response to the displayed eye exam material. The indications may be in the form of vocal or typed responses or any suitable input representing the user's identification of a test element of the eye exam. The indications may be in response to a prompt provided to the user by the mobile device or the computer 130. The prompt may include text on the display 170 or the computer 130 and/or an audio prompt. The prompt may display or state a command such as "please read the second line of characters on the eye chart."

The process 400 may include a step of determining a diagnosis or prescription based on the test subject's responses. The determination may be conducted automatically by software on the mobile device, the computer 130, or by the server. The determination may also be done by an optometrist that receives results of the test from the server 110, for example, over the Internet.

Process 400 ends at step 490.

In one alternative embodiment, a process 700, shown in FIG. 7, is provided for directing a test subject to two or more distances from the eye exam chart over the course of the examination.

Process 700 starts at step 710.

At step 720, indications are received from the test subject at a first distance in response to displayed eye examination material. The process 700 may occur after the process 400. In particular, the process 700 may be based on a user's results or partial results to an eye examination performed using process 700, for example, at step 470. In particular, if the user is at too great a distance to be able to properly read a displayed chart, based on the user's eye sight, the process 700 may be used to conduct an eye exam at a closer distance from the displayed eye chart.

At step 730, a second specified distance for the test subject is determined. This second distance may be determined in consideration of various factors. According to some embodiments, this determination may be made after ascertaining that the first distance is inappropriate. For example, if the user/test subject's eyesight is especially poor, then the user may not be able to engage in a meaningful eye examination from the first distance, and steps may be taken to have the user move closer. Alternatively, if the examination is too easy and therefore not allowing for appropriate evaluation and feedback, it may be required that a user move to a second distance that is greater than the first distance. In some embodiments, the step of determining and guiding a test subject to one or more additional distances may be in response to the requirements of a battery of tests. According to some embodiments, the determination of the second distance may be advantageous, where one eye test in a battery of tests provides more reliable results if performed at a second distance different from the first distance at which one or more tests were carried out.

In step 740, once a second distance is determined, the test subject may be guided to the second distance. Step 740 may be carried out in a manner corresponding to step 460 of the process 400.

At step 750, once the test subject has reached the new position, eye examination material is displayed. As discussed above, this material may be the same material as displayed when the test subject was at the first position or it may be new material.

At step 760, the steps of repositioning may be repeated as necessary to place the test subject in a third position, fourth position, and so on.

At step 770, process 700 ends.

According to another alternative embodiment, a final distance from the user to the test material is not predetermined. Instead, according to process 800, as shown in the flow chart in FIG. 8, the user moves to a distance of his choice from the monitor and undertakes an eye examination from that distance. The basis of the user's choice of the testing distance may be a variety of factors, such as limited room space. Or the user may choose the testing distance based on when an image displayed on the monitor becomes recognizable. Alternatively, the choice of distance may be arbitrary.

Figure 8:
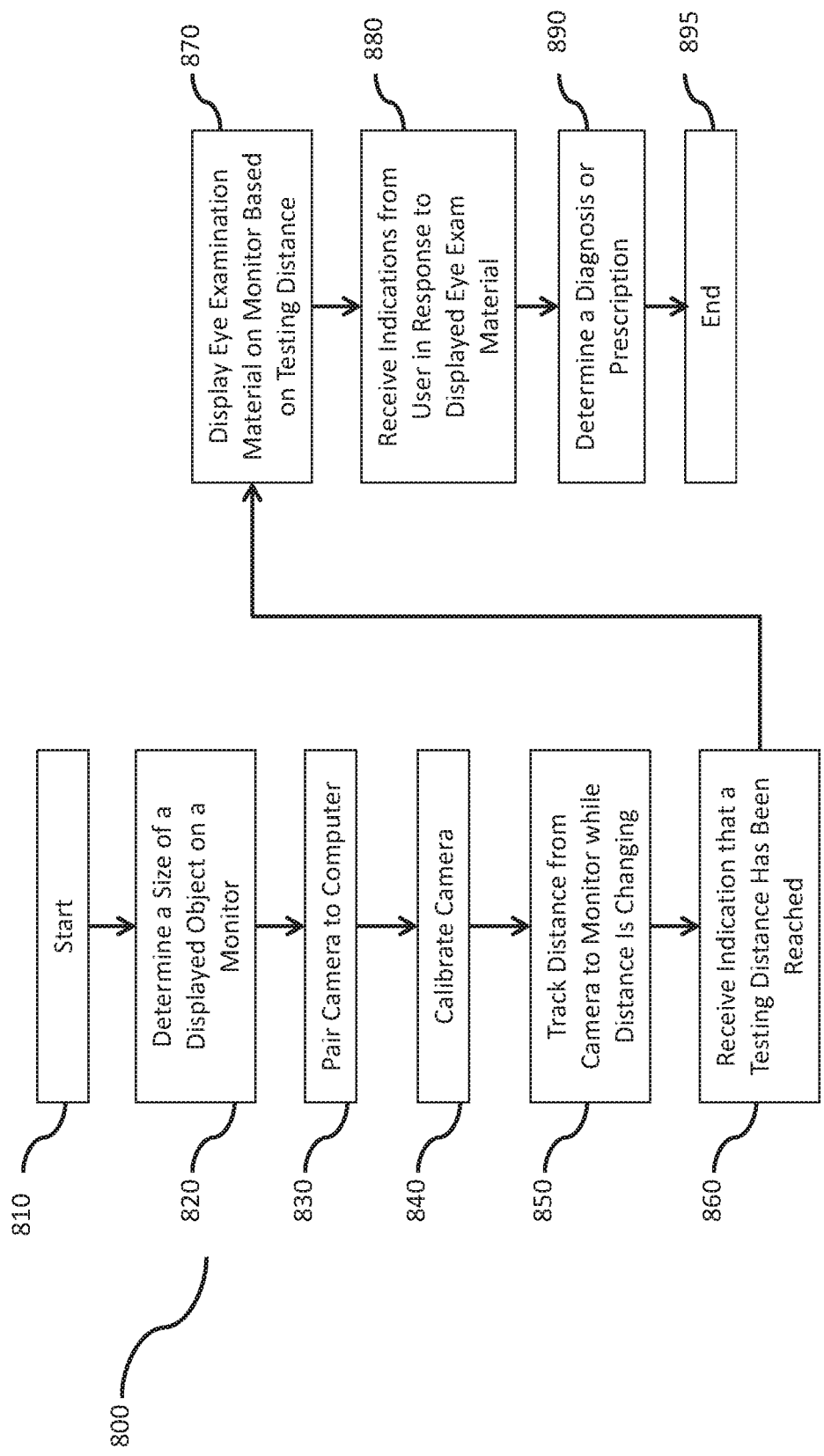
FIG. 8 is a flow chart of an alternative method for conducting an eye examination according to one or more embodiments.

As shown in the flow chart in FIG. 8, the initial steps 810, 820, 830, 840, and 850 are similar to the initial steps discussed with respect to process 400. However, instead of guiding a user to a specified distance from the monitor, the method incorporates a step 860 of receiving indication that a testing distance has been reached. Indication may be in the form of direct user input into the camera-enabled mobile device. Alternatively, indication may be in the form of the mobile device detecting no change in distance for a period of time, for example, three seconds or more.

Once the system has received an indication that the testing distance has been reached, the step 870 of displaying eye exam material on the monitor is carried out. Characteristics of the displayed material, such as their display size, are based on the determined testing distance. For example, the closer the user is to the monitor, the smaller the size of the displayed testing materials. Conversely, the further the user is from the monitor, the larger the display size. As shown in the flow chart in FIG. 8, steps 880, 890, and 895 are similar to the corresponding steps discussed with respect to process 400.

Figure 9:
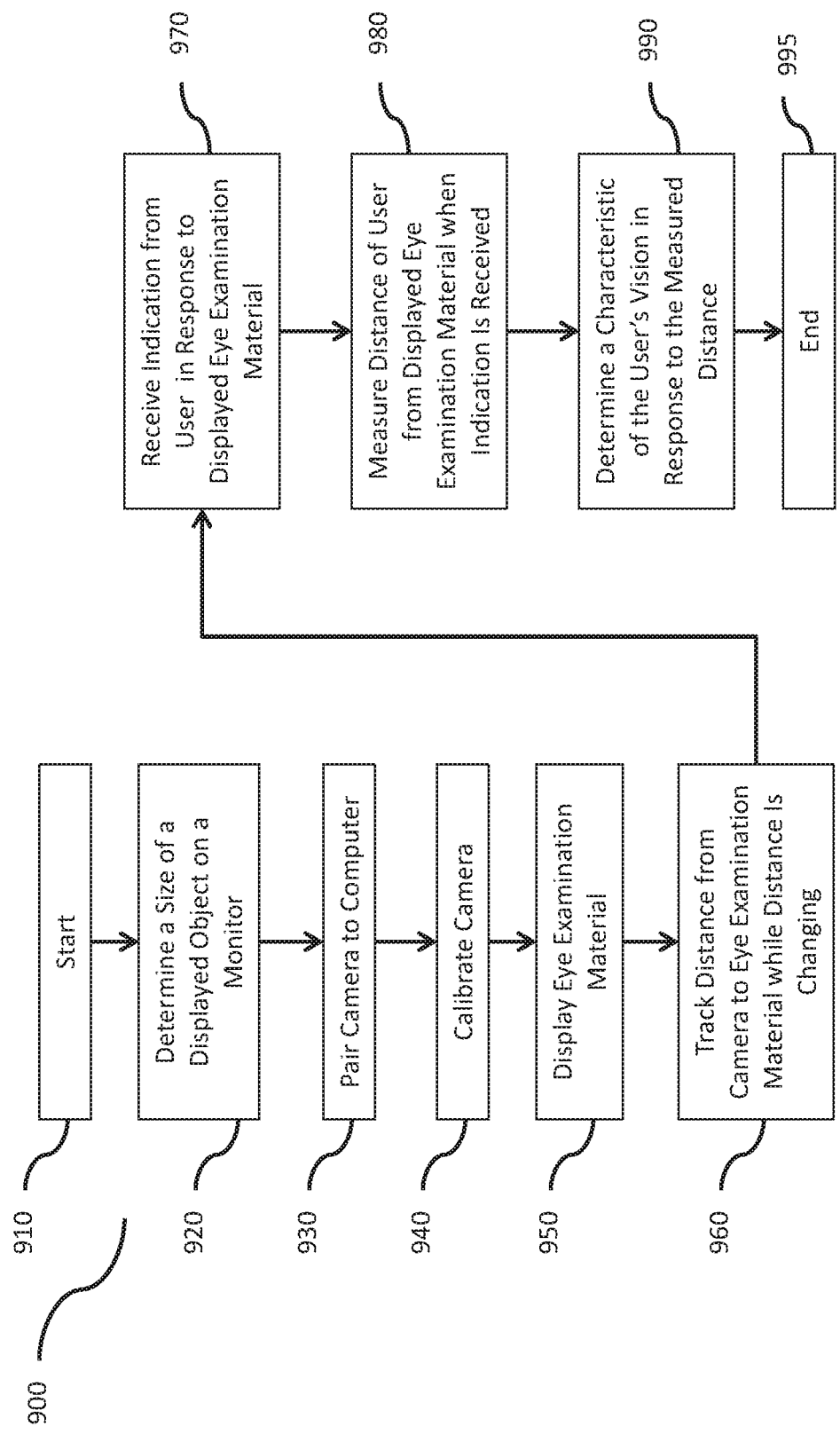
FIG. 9 is a flow chart of an alternative method for conducting an eye examination according to one or more embodiments.

According to another alternative embodiment, the user may be required to change distance from the screen in response to the material presented on the screen as part of a testing procedure. For example an image may be presented on the screen, and the user may be directed to walk to a distance where he can see this object clearly. That distance is noted by the system and aids in determining a characteristic of the user's vision. FIG. 9 shows a flow diagram of a process 900 incorporating such an embodiment. The initial steps 920, 930, and 940 are similar to corresponding steps discuss in relation to FIG. 4. In step 950, eye examination material is displayed. The user then moves to or from the displayed material, with the mobile device in hand, while, according to step 960, the distance to the eye examination material is tracked. The user then stops when reaching a certain distance, such as when the displayed object is clearly visible. According to step 970 of the process, the system then received indication from the user in response to the displayed eye examination material. The indication may be in the form of direct user input into the mobile device. Alternatively, indication may be in the form of the mobile device detecting no change in distance for a period of time, for example, three seconds or more. At this point, in step 980, the user's distance from the eye exam material is measured. This measured distance is then used, at least in part, to determine a characteristic of the user's vision, in step 990. Process 900 ends at step 995.

As discussed above, aspects and functions disclosed herein may be implemented as hardware or software on one or more of these computer systems. There are many examples of computer systems that are currently in use. These examples include, among others, network appliances, personal computers, workstations, mainframes, networked clients, servers, media servers, application servers, database servers and web servers. Other examples of computer systems may include mobile computing devices, such as cellular phones and personal digital assistants, and network equipment, such as load balancers, routers and switches. Further, aspects may be located on a single computer system or may be distributed among a plurality of computer systems connected to one or more communications networks.

For example, various aspects and functions may be distributed among one or more computer systems configured to provide a service to one or more client computers. Additionally, aspects may be performed on a client-server or multi-tier system that includes components distributed among one or more server systems that perform various functions. Consequently, examples are not limited to executing on any particular system or group of systems. Further, aspects may be implemented in software, hardware or firmware, or any combination thereof. Thus, aspects may be implemented within methods, acts, systems, system elements and components using a variety of hardware and software configurations, and examples are not limited to any particular distributed architecture, network, or communication protocol.

As shown in FIG. 1, the computer devices 110, 120, and 130 are interconnected by, and may exchange data through, communication a network 190. The network 190 may include any communication network through which computer systems may exchange data. To exchange data using the network 190, the computer systems 110, 120, and 130 and the network 190 may use various methods, protocols and standards, including, among others, Fibre Channel, Token Ring, Ethernet, Wireless Ethernet, Bluetooth, IP, IPV6, TCP/IP, UDP, DTN, HTTP, FTP, SNMP, SMS, MMS, SS7, JSON, SOAP, CORBA, REST and Web Services. To ensure data transfer is secure, the computer systems 110, 120, and 130 may transmit data via the network 190 using a variety of security measures including, for example, TSL, SSL or VPN.

Various aspects and functions may be implemented as specialized hardware or software executing in one or more computer systems. As illustrated in FIG. 1, the device 120 includes a processor 150, a memory 165, a camera 145, an output display 155, a data storage module 167, and an input device 160. The following description of the components of mobile device 120, may be generally understood to also apply to corresponding structure present in computer 130 or server 110.

The processor 150 may perform a series of instructions that result in manipulated data. The processor 150 may be a commercially available processor such as an Intel Xeon, Itanium, Core, Celeron, Pentium, AMD Opteron, Sun Ultra-SPARC, IBM Power5+, or IBM mainframe chip, but may be any type of processor, multiprocessor or controller. The processor 150 is connected to other system elements, including one or more memory devices 165, the camera 145, etc.

The memory 165 may be used for storing programs and data during operation of the device 120. Thus, the memory 165 may be a relatively high performance, volatile, random access memory such as a dynamic random access memory (DRAM) or static memory (SRAM). However, the memory 165 may include any device for storing data, such as a disk drive or other non-volatile storage device. Various examples may organize the memory 165 into particularized and, in some cases, unique structures to perform the functions disclosed herein.

The mobile device 120 also includes one or more interface devices such as input devices 160 and output devices 155. Interface devices may receive input or provide output. More particularly, output devices may render information for external presentation. Input devices may accept information from external sources. Examples of interface devices include keyboards, mouse devices, trackballs, microphones, touch screens, printing devices, display screens, speakers, network interface cards, etc. Interface devices allow the computer system 120 to exchange information and communicate with external entities, such as users and other systems.

The data storage 167 may include a computer readable and writeable nonvolatile (non-transitory) data storage medium in which instructions are stored that define a program that may be executed by the processor 150. The data storage 167 also may include information that is recorded, on or in, the medium, and this information may be processed by the processor 150 during execution of the program. More specifically, the information may be stored in one or more data structures specifically configured to conserve storage space or increase data exchange performance. The instructions may be persistently stored as encoded signals, and the instructions may cause the processor 150 to perform any of the functions described herein. The medium may, for example, be optical disk, magnetic disk or flash memory, among others. In operation, the processor 150 or some other controller may cause data to be read from the nonvolatile recording medium into another memory, such as the memory 165, that allows for faster access to the information by the processor 150 than does the storage medium included in the data storage 167. The memory may be located in the data storage 167 or in the memory 165, however, the processor 150 may manipulate the data within the memory 165, and then copy the data to the storage medium associated with the data storage 167 after processing is completed. A variety of components may manage data movement between the storage medium and other memory elements and examples are not limited to particular data management components. Further, examples are not limited to a particular memory system or data storage system.

Although the device 120 is shown by way of example as one type of a computer device upon which various aspects and functions may be practiced, aspects are not limited to being implemented on the device 120 as shown in FIG. 1. Various aspects and functions may be practiced on one or more computers having a different architectures or components than that shown in FIG. 1. For instance, the device 120 may include specially programmed, special-purpose hardware, such as for example, an application-specific integrated circuit (ASIC) tailored to perform a particular operation disclosed herein. While another example may perform the same function using a grid of several general-purpose computing devices running MAC OS System X with Motorola PowerPC processors and several specialized computing devices running proprietary hardware and operating systems.

The device 120 may include an operating system that manages at least a portion of the hardware elements included in the device 120. Usually, a processor or controller, such as the processor 150, executes an operating system which may be, for example, a Windows-based operating system, such as, Windows NT, Windows 2000 (Windows ME), Windows XP, Windows Vista or Windows 7 operating systems, available from the Microsoft Corporation, a MAC OS System X operating system available from Apple Computer, one of many Linuxbased operating system distributions, for example, the Enterprise Linux operating system available from Red Hat Inc., a Solaris operating system available from Sun Microsystems, or a UNIX operating systems available from various sources. Many other operating systems may be used, and examples are not limited to any particular implementation.

The processor 150 and operating system together define a computer platform for which application programs in high-level programming languages may be written. These component applications may be executable, intermediate, byte-code or interpreted code which communicates over a communication network, for example, the Internet, using a communication protocol, for example, TCP/IP. Similarly, aspects may be implemented using an object-oriented programming language, such as .Net, SmallTalk, Java, C++, Ada, or C # (C-Sharp). Other object-oriented programming languages may also be used. Alternatively, functional, scripting, or logical programming languages may be used.

Additionally, various aspects and functions may be implemented in a non-programmed environment, for example, documents created in HTML, XML or other format that, when viewed in a window of a browser program, render aspects of a graphical-user interface or perform other functions. Further, various examples may be implemented as programmed or non-programmed elements, or any combination thereof. For example, a web page may be implemented using HTML while a data object called from within the web page may be written in C++. Thus, the examples are not limited to a specific programming language and any suitable programming language could be used. Thus, functional components disclosed herein may include a wide variety of elements, e.g. executable code, data structures or objects, configured to perform described functions.

Embodiments described above utilize a process for determining distance between two objects in conjunction with the performance of an eye exam. Other embodiments may be used to determine distance for a number of different applications including: providing directions or orientation guidance for use in a retail store or other location to allow a user to find a specific location or object relative to the screen; games in which a player must throw something at a target a certain distance away from their present location; visualizing the size of an object that might be later placed in that space (such as furniture in a room); or other applications which require a user to determine absolute distances or sizes. Having thus described several aspects of at least one example, it is to be appreciated that various alterations, modifications, and improvements will readily occur to those skilled in the art. For instance, examples disclosed herein may also be used in other contexts. Such alterations, modifications, and improvements are intended to be part of this disclosure, and are intended to be within the scope of the examples discussed herein. Accordingly, the foregoing description and drawings are by way of example only.

What is claimed is:

1. A process for conducting an eye examination using a mobile device, the process comprising:
    capturing a first image of an object using a camera of a mobile device set to a fixed focusing distance;
    determining, with reference to the first image, an absolute size of the object;
    capturing a second image of the object using the camera of the mobile device;
    determining, with reference to the second image, a distance from the mobile device to the object;
    providing an indication via the mobile device to move the mobile device relative to the object; and
    receiving input from the mobile device in response to an eye examination program.

2. The method of claim 1, wherein the object is an optotype displayed in connection with the eye examination program.

3. The method of claim 1, wherein the object is a test pattern.

4. The method of claim 1, wherein determining, with reference to the first image, the absolute size of the object further comprises determining a first image size of the object in the first image.

5. The method of claim 4, wherein determining, with reference to the first image, the absolute size of the object is performed with reference to the first image size of the object in the first image, a focal length of the camera of the mobile device, a second distance between a lens and a focal plane of the camera, and a third distance from the lens at which the object is in optimal focus.

6. The method of claim 1, wherein determining, with reference to the second image, the distance from the mobile device to the object further comprises determining a second image size of the object in the second image.

7. The method of claim 6, wherein determining, with reference to the second image, the distance from the mobile device to the object is performed with reference to the second image size of the object in the second image, the absolute size of the object, and the focal length of the camera of the mobile device.

8. The method of claim 1, wherein providing the indication via the mobile device to move the mobile device relative to the object comprises providing an indication via the mobile device to move the mobile device in a direction relative to the object.

9. The method of claim 1, wherein providing the indication via the mobile device to move the mobile device relative to the object comprises providing an indication via the mobile device to move the mobile device to a second distance from the object.

10. The method of claim 9, wherein the second distance corresponds to an optimal distance for conducting the eye examination program.

11. A mobile device comprising:
a camera;
a user interface comprising a visual display;
a memory comprising instructions; and
a processor coupled to the camera, the processor configured to execute the instructions to:
    capture a first image of an object using the camera set to a fixed focusing distance;
    determine, with reference to the first image, an absolute size of the object;
    capture a second image of the object using the camera;
    determine, with reference to the second image, a distance from the mobile device to the object;
    provide, via the user interface, an indication via the display to move the mobile device relative to the object; and
    receive, via the user interface, input from the mobile device in response to an eye examination program.

12. The mobile device of claim 11, wherein the processor is further configured to execute the instructions to determine, with reference to the first image, the absolute size of the object further comprises the processor being configured to determine a first image size of the object in the first image.

13. The mobile device of claim 12, the camera comprising a lens having a focal length and a focal plane, wherein the processor is further configured to execute the instructions to determine, with reference to the first image, the absolute size of the object is performed with reference to the first image size of the object in the first image, the focal length, a second distance between the lens and the focal plane, and a third distance from the lens at which the object is in optimal focus.

14. The mobile device of claim 11, wherein the processor being configured to execute the instructions to determine, with reference to the second image, the distance from the mobile device to the object further comprises the processor being configured to execute the instructions to determine a second image size of the object in the second image.

15. The mobile device of claim 14, the camera comprising a lens having a focal length, wherein the processor being configured to determine, with reference to the second image, the distance from the mobile device to the object is performed with reference to the second image size of the object in the second image, the absolute size of the object, and the focal length.

16. The mobile device of claim 11, wherein the processor is further configured to execute the instructions to provide the indication via the display to move the mobile device relative to the object comprises the processor further configured to execute the instructions to provide a second indication via the display to move the mobile device in a direction relative to the object.

17. The mobile device of claim 11, wherein the processor is further configured to execute the instructions to provide the indication via the display to move the mobile device relative to the object comprises the processor further configured to execute the instructions to provide a second indication via the display to move the mobile device to a second distance from the object.

18. The method of claim 17, wherein the second distance corresponds to an optimal distance for conducting the eye examination program.

\* \* \* \* \*